United States Patent
Mueller et al.

(10) Patent No.: US 8,672,965 B2
(45) Date of Patent: Mar. 18, 2014

(54) NUCLEUS REPLACEMENT BASED ON INJECTABLE PVA GELS

(75) Inventors: Rolf Mueller, Zurich (CH); Federico Innerebner, Zurich (CH); Thomas Steffen, Worb (CH); Norbert Boos, Wernetshausen (CH)

(73) Assignee: InnoGEL AG, Huenenberg (CH)

( * ) Notice: Subject to any disclaimer, the term of this patent is extended or adjusted under 35 U.S.C. 154(b) by 319 days.

(21) Appl. No.: 12/995,146

(22) PCT Filed: May 27, 2009

(86) PCT No.: PCT/CH2009/000178
§ 371 (c)(1),
(2), (4) Date: Nov. 29, 2010

(87) PCT Pub. No.: WO2009/143646
PCT Pub. Date: Dec. 3, 2009

(65) Prior Publication Data
US 2011/0077684 A1    Mar. 31, 2011

(30) Foreign Application Priority Data

May 27, 2008    (WO) ................ PCT/CH2008/000236

(51) Int. Cl.
*A61B 17/03*    (2006.01)
*B65D 85/00*    (2006.01)
*A61F 2/02*    (2006.01)
*A61K 49/04*    (2006.01)

(52) U.S. Cl.
USPC .......... 606/214; 206/524.1; 523/113; 424/9.4

(58) Field of Classification Search
USPC ............... 606/214, 108; 206/524.1; 523/113; 623/17.11, 17.16, 1.23, 1.11, 1.35; 128/898; 424/486, 9.4; 524/503
See application file for complete search history.

(56) References Cited

U.S. PATENT DOCUMENTS

| | | | |
|---|---|---|---|
| 3,933,587 A | 1/1976 | Maeda et al. | |
| 7,112,205 B2* | 9/2006 | Carrison | 606/92 |
| 7,214,245 B1 | 5/2007 | Marcolongo et al. | |
| 7,708,979 B2* | 5/2010 | Lowman et al. | 424/9.4 |
| 2001/0029399 A1* | 10/2001 | Ku | 623/1.23 |
| 2006/0270781 A1* | 11/2006 | Ruberti et al. | 524/503 |

FOREIGN PATENT DOCUMENTS

| | | |
|---|---|---|
| WO | 9210982 | 7/1992 |
| WO | 2005017000 | 2/2005 |
| WO | 2006021122 | 3/2006 |
| WO | 2007050744 | 5/2007 |
| WO | 2008031235 | 3/2008 |

OTHER PUBLICATIONS

Rebecca A. Bader et al., Rheological characterization of photopolymerized poly(vinyl alcohol) hydrogels for potential use in nucleus pulposus replacement, issued on Jul. 6, 2007, appears in Journal of Biomedical Materials Research Part A, p. 494-p. 501.

(Continued)

*Primary Examiner* — Pedro Philogene
(74) *Attorney, Agent, or Firm* — J.C. Patents

(57) ABSTRACT

The invention relates to novel polyvinyl alcohol (PVA) gels which gelate in situ and are suitable for nucleus (gel bodies of the intervertebral disks) replacement, and to a process and to an apparatus for administration thereof, to the use thereof and to a vessel which comprises an inventive PVA gel.

10 Claims, 7 Drawing Sheets

(56) References Cited

OTHER PUBLICATIONS

Jonathan Thomas et al, "Novel associated hydrogels for nucleus pulposus replacement", issued on 2003, appears in Journal of Biomedical Research, p. 1329-p. 1337.

Takashi Noguchi et al, "Poly(vinyl alcohol) Hydrogel as an artificial articular cartilage: Evaluation of Biocompatibility", issued on 1991, appears in Journal of Applied Biomaterials, vol. 2, p. 101-p. 107.

* cited by examiner

NUCLEUS REPLACEMENT BASED ON INJECTABLE PVA GELS

CROSS-REFERENCE TO RELATED APPLICATION

This patent application claims priority benefit of a PCT application serial no. PCT/CH2009/000178, filed on May 27, 2009. The PCT application serial no. PCT/CH2009/000178 also claims priority benefit of a PCT application serial no. PCT/CH2008/000236, filed on May 27, 2008. All disclosure of the PCT application serial no. PCT/CH2009/000178 and the PCT application serial no. PCT/CH2008/000236 are incorporated herein by reference.

The invention relates to novel polyvinyl alcohol (PVA) gels which gelate in situ and are suitable for nucleus (gel bodies of the intervertebral discs) replacement, and to a method and to a device for the application thereof, to the use thereof and to a vessel which contains a PVA gel according to the invention.

PRIOR ART

T. Noguchi, T. Yamamuro et al. have shown in *Journal of Applied Biomaterials* Vol. 2, 1991, pages 101-107 that hydrogels based on polyvinyl alcohol (PVA) can be produced with the consistency of biological tissue and cartilage and have an excellent stability and biocompatibility in the living organism, which on the one hand is founded in the high water content of these gels and on the other hand in the macromolecule itself, which is experienced by the organism as a result of the numerous hydroxyl groups similarly to water. Therefore, PVA gels are positively predestined for applications in the living organism.

In *Journal of Biochemical Materials Research Part A* Vol. 86a No. 2, 2007, pages 494-501, R. A. Bader and W. E. Rochefort give an example for the application of a PVA hydrogel as synthetic joint cartilage. Here, however, the PVA gel is cross-linked by irradiation.

It is known from WO 2005/017000 A1 to use PVA gels as nucleus replacement. However, these require the addition of a gelation medium for hardening, such as for example a salt or other problematic chemicals. In a similar manner, WO 2007/050744 describes a PVA gel as nucleus replacement, the hardening of which is initiated by the addition of a cross-linking agent.

U.S. Pat. No. 7,214,245 B1 discloses a hydrogel based on a blend of PVA and PVP (polyvinyl pyrollidone) for use as nucleus replacement. In *Journal of Biomedical Research Part A* Vol. 67a No. 4, 2003, pages 1329-1337, J. Thomas et al. investigate such hydrogels on the basis of PVA and PVP. They arrive at the result that these gels tend to deliver PVP chains, which results in an intensive swelling and poor mechanical characteristics.

WO 92/10982 A1 describes a nucleus replacement of a PVA gel. This is prepared outside the body in a mixture of water and an organic solvent and hardened in a mould. The organic solvent must then be exchanged by water, before the nucleus replacement can be inserted into the body.

In the nucleus replacement, the viscosity of the mass which is to be injected is a crucial parameter in order to obtain a good filling of a cleared intervertebral disc. With sufficiently high viscosity, a good filling can be achieved by a pressure being able to be built up within the intervertebral disc during the injection. In so doing, the original height of the intervertebral disc can even be at least partially produced. When the injection is ended and the injection needle is withdrawn, the deposited mass no longer flows back, owing to the high viscosity. In the case of viscosities which are too low, the said pressure can not be built up and the deposited mass can flow out from the cavity before it has gelated sufficiently, in order to prevent flowing. Such a PVA gel gelating in situ, i.e. at the location of use, having a viscosity which is too low, is known from WO 2006/021122 A2.

The prevailing criterion for failure in solutions hitherto in the field of nucleus replacement is the extrusion, i.e. the at least partial emergence of the gel from the nucleus space.

It is therefore an object of the present invention to provide an improved PVA gel gelating in situ, which as regards its processing behaviour, in particular concerning the viscosity and the gelation speed, and concerning its end characteristics, in particular E-modulus and extrusion behaviour, is tailored to the application as injectable gel for the replacement of nucleus material by means of a minimally invasive method.

BRIEF DESCRIPTION OF THE INVENTION

This object is solved according to the invention by a PVA gel which gelates in situ and which has PVA and water as swelling agent. The water content W of the PVA gel is in the range of 52-64% by weight. The upper limit for the weight average of the degree of polymerisation Pw of the PVA is given by the relationship Pw=W·150–5500, and the lower limit for the weight average of the degree of polymerisation Pw of the PVA is given by the relationship Pw=W·90–3800. The viscosity of the molten gel at a temperature in the range of 30 to 100° C. is in the range of 60-2000 Pas, wherein viscosity is to be understood in the sense of the invention as the dynamic viscosity.

With a decreasing water content, the viscosity, like the gelation speed, increases. As conventional PVA/water mixtures gelate comparatively slowly, an exerting of influence on this parameter is of great importance. This is because a treated intervertebral disc should be able to be stressed at least minimally at the latest 1 h after the operation. The lower limit of the water content results on the one hand through the viscosity which becomes too high in the case of water contents which are too low; the upper limit of the water content results from the viscosity which becomes too low and from the gelation speed which becomes too low. The lower limit for the water content of the PVA gel in % by weight therefore preferably is 54, particularly preferably 55, most particularly preferably 56. The upper limit for the water content of the PVA gel in % by weight preferably is 62, particularly preferably 61, most particularly preferably 60. The water content results from the weight of the water divided by the weight of the PVA gel. When the gel contains a filler which is present in a separate phase, this is not counted for the gel.

The weight average of the degree of polymerisation Pw of the PVA results as the sum wi times Pwi, wherein wi is the weight fraction of the species PVAi with the weight average of the degree of polymerisation Pwi:

$$Pwi=\Sigma(wi \cdot Pwi)$$

If, for example, the PVA consists of one type of PVA, then Pw is the Pw of this PVA type. If the PVA consists of two types of PVA, wherein PVA1 is 40% by weight and PVA2 is 60% by weight of the PVA, then Pw=0.4×Pw1+0.5×Pw2.

In a preferred embodiment, the lower limit of Pw with a water content W of 50% by weight is 750, whereas with a water content W of 70% by weight it is 2600. With water contents of between 50 and 70%, linearly interpolated values apply, i.e. Pw=W·92.5–3875. In a particularly preferred embodiment, the lower limit of Pw with a water content W of 50% by weight is 800, whereas with a water content of 70% by weight it is 2700, i.e. Pw=W·95–3950. In a particularly preferred embodiment, the lower limit of Pw with a water content W of 50% by weight is 900, whereas with a water content of 70% it is 2800, i.e. Pw=W·95–3850.

In a preferred embodiment, the lower limit of Pw with a water content W of 50% by weight is 1700, whereas with a water content of 70% it is 4500. With water contents of between 50 and 70%, linearly interpolated values apply, i.e. Pw=W·150–5500. In a particularly preferred embodiment, the lower limit of Pw with a water content W of 50% is 1400, whereas with a water content of 70% it is 4000, i.e. Pw=W·130–5100. In a most particularly preferred embodiment, the lower limit of Pw with a water content W of 50% is 1200, whereas with a water content of 70% it is 3500, i.e. Pw=W·115–4550.

In a preferred embodiment, the viscosity of the molten gel with a temperature in the range of 40 to 80° C., more preferably in the range of 45 to 70° C., most preferably 50 to 65° C., is in the range of 60-2000 Pas, wherein viscosity is understood in the sense of the invention to mean the dynamic viscosity.

The subject matter of the invention is a non-chemically, but physically cross-linking gel on the basis of PVA. The gel according to the invention is able to be processed well, has an accelerated hardening behaviour compared with conventional PVA gels and shows no extrusion, even under massive loadings which have been applied to repaired human intervertebral discs in the biomechanical laboratory. With an increasing of the stress, the end plates of the intervertebral discs broke without gel having previously extruded. Furthermore, the invention describes concepts and apparatus which are suitable and necessary in order to use the PVA gels in practice.

Likewise, the gelation speed increases with an increasing viscosity of the gel, which is essential for a successful use, because for example with a use in the field of nucleus replacement the gel should be able to be at least slightly stressed after approximately 15 min.

PVA mixtures with weight average of the degree of polymerisation Pw within the defined limits can be obtained for example in that one type of PVA with a suitable Pw is used or two types with different Pw and proportions, so that the combination is within the defined limits for Pw, or three or more types with different Pw and proportions, so that the combination is within the defined limits for Pw. Preferably, the mixtures have at least two types with different Pw, wherein the one type, PVA1 has an weight average of the degree of polymerisation Pw of >1500, preferably >1700, more preferably >2000, and the other type, PVA2 of <1500, preferably <1700, more preferably <2000. The lower limit for the proportion of PVA1 in % by weight in relation to PVA1 and PVA2 is 5%, preferably 20%, more preferably 30%, most preferably >35%. The upper limit for the proportion of PVA1 in % by weight in relation to PVA1 and PVA2 is 60, preferably 55, more preferably 50, most preferably 45.

The average gelation speed during the first 24 hours hardening time can be determined by means of a compression test, wherein the E-modulus is investigated as a function of time. Preferably, this gelation speed in MPa per hour is >0.01, preferably >0.03, more preferably >0.06, most preferably >0.08. A gelation speed >0.10 is most particularly preferred.

Preferably, E-modulus in MPa of the fully hardened PVA gels is >0.25, preferably >0.5, more preferably >0.75, most preferably >1.0. The upper limit for the E-modulus in MPa of the fully hardened PVA gels is <10, preferably <7.5, more preferably <6.5, most preferably <5.5.

An important characteristic of the PVA gels for the nucleus application is the restoring behaviour after lengthy stressing in water or Ringer's solution. In a preferred embodiment, the height of a PVA cylinder which was stressed for 12 h with 0.7 MPa was restored within the next 4 days to >70%, preferably to >75%, more preferably to >80%, most preferably >83%.

Preferably, the PVA gels according to the invention, after gelation at 25° C. have a melt peak measured in DSC (in accordance with DIN 53765) with a peak temperature (temperature of the maximum) in the range of 80-95° C. Furthermore, it is preferred that the PVA gels after gelation at 25° C. additionally have a melt peak measured in DSC with a peak temperature (temperature of the maximum) in the range of 45-65° C.

CHARACTERISATION OF THE PVA

Figure 1:
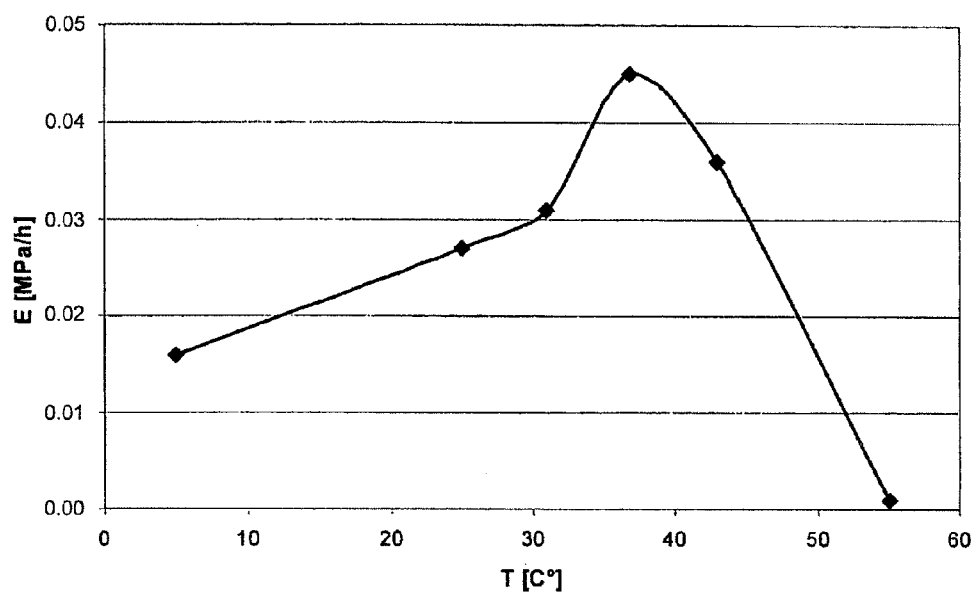
FIG. 1 represents the result of a measurement of the E-modulus of a PVA gel which has been produced according to example 1 of the invention, but with a water content of 60.1%.

The same requirements are made of the polyvinyl alcohols PVA1, PVA2 and, optionally further types of PVA, which make possible as good an ability as possible of the PVA to crystallize and a high stability of the crystallites. Therefore, deviations from the ideal structure [—$CH_2$—CHOH—]$_n$ are to be kept as small as possible proportionately.

Preferably, the degree of hydrolysis (H) of the PVA in mol-% is >98, preferably >99, more preferably >99.2, more preferably >99.4. In a particularly advantageous embodiment, H is >99.85, preferably >99.9, more preferably >99.95, most preferably >99.98. In the range of these high degrees of hydrolysis, only a slight increase has a surprisingly clear effect on the end characteristics of the gel.

A content (G) of 1,2-glycol in mol-% of <3 is advantageous, preferably <1, more preferably <0.5, most preferably <0.2.

A number of short-chain branches of the PVA per monomer unit of $<10^{-2}$ is advantageous, preferably $<10^{-3}$, more preferably $<10^{-4}$, most preferably $<10^{-6}$.

Further disturbances to the regularity such as carbonyl groups in the chain are likewise undesired; in conventional PVA their proportion with typically <0.02 mol-% is, however, negligible.

With regard to tacticity, an atactic conformation is preferred compared with an isotactic one, a syndiotactic conformation is most preferred, or respectively as high a proportion as possible of syndiotactic diads. The tacticity of PVA is established by the type of monomers, with which the precursor polymer, from which the PVA is obtained, is polymerised, and by the reaction conditions in this polymerisation, wherein with a decreasing temperature during the polymerisation the syndiotactic proportion increases.

If the precursor polymer is polymerised from vinyl acetate derivatives of the type $CH_2=CHOCOR$, wherein R may be for example H, $CH_3$, $C_3H_7$, $C_4H_9$, $CClH_2$, $CCl_3$, $CF_3$, $C_4H_5F_4$, $C_6H_7F_6$ or $C_6H_5$, then the proportion of syndiotactic diads increases with the volume of the group R (whereas the 1,2-glycol content advantageously decreases) and the tacticity obtained in the precursor polymer is maintained in the subsequent hydrolysis to the PVA. Therefore, monomers for the polymerisation of the precursor polymer such as vinyl acetate, vinyl chloroacetate, vinyl dichloroacetate, vinyl bromoacetate, in particular vinyl trifluoroacetate are preferred.

If the precursor polymer is produced from aliphatic vinyl acid esters, high proportions of syndiotactic diads are likewise obtained, whilst the resulting PVAs in addition have very low 1,2-glycol contents. Examples are vinyl formate, vinyl propionate, vinyl butyrate, vinyl pivalate. Very high molecular weights can also be achieved by means of vinyl pivalate.

Fully hydrolysed PVAs obtained from polyvinyl acetate are also soluble in water with high degrees of crystallisation at 100° C., whereas fully hydrolysed PVA, the precursor polymers of which were produced from vinyl acetate derivatives with voluminous group R (e.g. vinyl trifluoroacetate) or from aliphatic vinyl acid esters (e.g. vinyl fromate, vinyl pivalate) can be obtained in insoluble form as a result of the low 1,2-glycol content and the high proportion of syndiotactic diads even at 100° C. From this, the importance of these parameters for the crystallisability and the stability of the crystallites becomes clear.

Concerning the polydispersity P of the three previously mentioned PVA types, P<5 is preferred, particularly preferably <3, most particularly preferably <2.

As regards the topology, conventional PVAs are predominantly linear, long-chain branches then occur rarely, if at all, in conventional PVAs. Almost complete or complete linearity is preferred in short-chain PVA2s, with this condition being practically always fulfilled, whereas long-chain PVA1s do not necessarily have to be as linear as possible, a proportion of long-chain branches can even be advantageous in PVA1, if the length of these side chains has a degree of polymerisation DP>40.

Further Polymers

In addition to PVA, the PVA gel for modification of the characteristics and for specific applications can contain further polymers, preferably synthetic polymers, in particular polycarbonates, polyacrylates and polymethacrylates, polyethylene glycols, polyethylene oxides, polyvinyl pyrrolidones, polycaprolactones or polymers of natural origin, preferably hydrocolloids and polysaccharides, in particular starch and starch derivatives. Such further polymers are preferably used in proportions in % by weight in relation to 100% by weight PVA gel of 0 to 30, particularly preferably 0 to 15, most particularly preferably 1 to 10.

Additives

Simple fillers and functional fillers or respectively active substances or substances producing X-ray contrast such as for example barium sulphate, are designated as additives. Substances producing X-ray contrast are preferably used in proportions in % by weight of 10 to 50, particularly preferably of 25 to 40, respectively in relation to 100% by weight PVA gel.

Applications

As the PVA gels according to the invention can be obtained with a wide range of mechanical characteristics, a whole series of applications are possible. On the one hand, previous PVA gels are advantageously replaced in all applications, because the new gels are very much simpler to produce (pourability, gel-forming temperature>0° C., stability) and have at least equally good mechanical characteristics. On the other hand, the new gels, in particular as gels gelating in situ, open up remarkably interesting applications in the field of biomedicine (e.g. tissue and scaffold engineering) and in particular in orthopaedics. Tissues, gels, cartilage, in particular tendons, bands, joint surfaces, menisci, nerve sheaths, urethrae, heart valves, gel bodies of the intervertebral discs (nucleus) can be replaced or repaired. In the field of intervertebral discs and vertebrae, in particular the following specific applications come into consideration: total disc replacement, nucleoplasty, facet replacement, segment replacement, vertebroplasty, kyphoplasty, lordoplasty. The gels according to the invention are most particularly suitable for the field of nucleus replacement. Further applications are in the field of cosmetic or respectively plastic surgery, where the gels constitute an alternative to silicone implants.

Application Methods

For the application of the PVA gel, the gel is processed according to the invention after a storage period by a method which has the following steps:
a) Heating for a time t1 to a temperature T1
b) Waiting for a time t2 at the temperature T1
c) Cooling for a time t3 to a temperature T2
d) Injection at a temperature T3
e) Hardening at body temperature During steps a) and b), the PVA gel is preferably situated in a closed vessel which is opened during or after step c). The vessel is preferably an ampoule.

Heating

The temperature T1 is sufficiently high so that the PVA gel is at least partially, preferably completely, melted. In a preferred embodiment, T1 in ° C. is >85, more preferably >95, most preferably >97. The temperature T1 can be reached by the temperature being continuously increased to T1, or by active regulation by firstly a slightly higher temperature being reached and then cooling taking place to T1.

The temperature T1 can also be set to a value distinctly above 100° C., because PVA has a good heat resistance. In a preferred embodiment, T1 in ° C. is <200, preferably <140, more preferably <110, most preferably <105.

The temperature T1 does not necessarily have to be constant, it can also have a profile within the indicated limits.

The time t1 can be of any desired length per se. In a preferred embodiment t1 in min is <30, preferably <20, more preferably <15, most preferably <5.

Waiting

The time t2 can likewise be of any desired length per se, in particular the molten gel can be held ready at T1. In a preferred embodiment, t1 in min is <30, preferably <20, more preferably <10, most preferably <5. The time t2 can in particular also be 0 min. The temperature T1 can be constant during the waiting time t2 or can have a profile.

Cooling

The temperature T2 in ° C. is in the range 30-80, preferably 45-70, more preferably 50-65, most preferably 50-60. It can be set by continuous cooling or by active regulation.

In a preferred embodiment, the cooling time t3 in min is <30, preferably <15, more preferably <10, most preferably <5. The shorter the cooling time, the longer the injection time can be, which is critical.

Injection

The injection takes place at a temperature T3, wherein T3 in ° C. is in the range 30-80, preferably 45-70, more preferably 50-65, most preferably 50-60.

In a preferred embodiment, the entire preparation time of the PVA gel in min, beginning with the heating and ending with the end of the cooling is as short as possible, and is <30, preferably <20, more preferably <10, most preferably <5.

Vessel for the PVA Gel Gelating in Situ

The invention further relates to a closed vessel containing the PVA gel gelating in situ according to the invention. The closed vessel is preferably an ampoule.

Preferably, the closed vessel comprises end caps on one side or both sides, a membrane, preferably a rubber membrane, and a plunger which is sealed in a sliding manner. The sliding seal can be effected for example by a ring seal or an O-ring. An end cap prevents the plunger from being pressed out from the ampoule. The plunger has a central recess.

Injection Device

In addition, the invention relates to an injection device, comprising a cannula mounted on the front side of the injection device, the end of which, projecting into the interior of the injection device, has cutting edges, a screw cap placed on the rear side of the injection device, which has a central threaded hole, a threaded pin which is guided through the central threaded hole of the screw cap, a manual rotary knob which is arranged on the threaded pin, with a cavity being formed between the front side and the rear side of the injection device, which is configured so that it can receives a closed vessel according to the invention.

The injection device is preferably configured in order to measure the injection pressure on injecting a PVA gel through the cannula.

EXAMPLES

Analytic Methods

Measurement of the Mechanical Characteristics

The mechanical characteristics were measured in the "unconfined compression" mode, i.e. the extension of the test piece was not restricted in the direction perpendicularly to the compression direction.

Apparatus: Instron 5542, load cell: 500 N. Software: Series IX, Automated Materials Testing System 50.00
Test piece: Cylinder with diameter of 11.8 mm and a height of 12 mm
Compression speed: 10 mm/min
Temperature: 25° C.

The determining of the E-modulus took place by mean increase of the tension-compression curve in the range of 0.20-0.25 mm/mm.

Restoring Behaviour (Recovery)

Cylindrical gels with a diameter of 11.8 mm and a height H0 of 12 mm were stored at 25° C. in water (or respectively Ringer's solution, when the gel was produced with Ringer's solution) for 4 days, after which the height H1 was measured. Then a load of 0.7 MPa was applied (typical load on an intervertebral disc) and kept constant for 12 h (stress during the day), with the gel body being compressed. Thereafter, the gel body was relieved of its load and stored for 4 days at 25° C., with a height H2 occuring asymptotically. The restoring or respectively recovery in % was obtained as $100 \cdot H2/H0$.

Water Content

The water content of PVA samples was obtained by drying in an oven at 90° C. with phosphorus pentoxide as drying medium for 48 h, with the sample size being respectively <3 mm. The water content was obtained as weight loss divided by the original weight.

DSC

Apparatus: DSC 7 of Perkin Elmer,
Measurement according to DIN 53765, 10° C./min.

Viscosity (Dynamic Viscosity)

For the measurement of the viscosities, PVA gels were firstly melted for 5 min at 100° C. in a syringe. The syringe had a cross-section of 111 mm$^2$ and an internal diameter of 11.9 mm. The length of the cannula was 5 inches (127 mm) and had an internal diameter of gauge 8 (3.2 mm). Thereafter, the syringe with contents was introduced into a water bath with a temperature of 50 or respectively 60° C. and was stored again there. The contents were than ejected at 1.41 mm/s for 8 seconds.

Pressure measurement: MTS 858 Mini Bionix of MTS Systems Co. (Eden Prairie, Minn.), stroke-controlled, equipped with a 10 KN load cell and controlled by Testware-SX 4.0B.

From the measured pressures, dynamic viscosities were obtained by means of calibration. The calibration was carried out at 25° C. with viscosity standards of Brookfield Engineering Laboratories Inc. (USA) and with exactly the same set-up as for the PVA gels. The viscosity standards at 25° C. had viscosities in mPas of 95360, 201363, 381940, 546800.

Comparative Examples

PVA gels were produced according to Examples 2, 6, 7, 8 and 9 of WO 2006/021122. For this, a PVA1 (degree of polymerisation DPn=2500, Pw1=5000) was mixed with a PVA2 (DPn=180; Pw2=360 or respectively DPn=300, Pw2=600). The proportion of PVA1 with respect to PVA1 plus PVA2, the weight average of the degree of polymerisation Pw of the PVA, the water content of the obtained gels, and the viscosity of the gels at 50° C. can be seen from Table 2. It can be seen that the comparative gels in fact have a water content in accordance with the invention, but differ with regard to the Pw of gels according to the invention. This leads to very low viscosities, which are also listed in Table 2, so that the comparative gels with use as nucleus replacement would flow out of the cavity before they are sufficiently gelated, in order to prevent flowing.

Example 1

30.05 g PVA1 (Pw=4300) with a water content of 8.8% by weight was dissolved with 106.46 g Ringer's solution at 98° C. in a closed flask with agitation for 50 min. Then with a constant temperature 38.850 g PVA2 (Pw=600) with a water content of 6.6% was added and the mixture was agitated for 25 min until the mixture was homogeneous and completely dissolved. The proportion of PVA1 in relation to PVA1 plus PVA2 was 40.3% by weight, the water content was nominally 62.2% by weight and actually (as a result of loss) 61% by weight. 34 g barium sulphate powder was then added, resulting in 16.8% by weight barium sulphate in relation to the entire mixture, and the mixture was homogenised by agitation. The mixture was then filled into test tubes and the test tubes were centrifuged and closed in an air-tight manner. The gel was stored in this state. For further processing, the gel in the test tube was melted at approximately 98° C. and removed, respectively for the production of cylinders for the analysis of the mechanical characteristics or for injection into cleared intervertebral discs for cadaver tests.

The viscosity of the gel after melting at 100° C. and after 5 min storage at 60° C. was 280 Pas. The hardening speed during the first 24 h measured on the E-modulus in unconfined compression and at 37° C. was 0.027 MPa/h and the E-modulus in unconfined compression after complete hardening at 37° C. was approximately 3 MPa. The restoring (recovery) was 77%.

The result of a measurement of the E-modulus of a gel which has been produced in an analogous manner, but with a water content of 60.1% is represented in FIG. 1. It can be seen that the hardening at 37° C. was in the range of the maximum hardening speed.

For the cadaver tests, intervertebral discs were cleared, the cannula for the injection of the PVA was introduced by means of 6 mm dilatation technique, and the PVA was thus injected. The intervertebral discs were stored in physiological saline solution for 24 h, before the mechanical loading was applied. The biological system was stabilised by antibiotics. The mechanical loading was 1400N axial load (corresponds to approximately 1.5 MPa pressure onto the intervertebral disc) and with a bending of up to ⅔ of physiological bending. The mode was alternating between flexion-compression, lateral bending-compression, extension-compression. Extrusion was not observed in any of the examined intervertebral discs. The results are listed in Table 1.

Example 2

Figure 2:
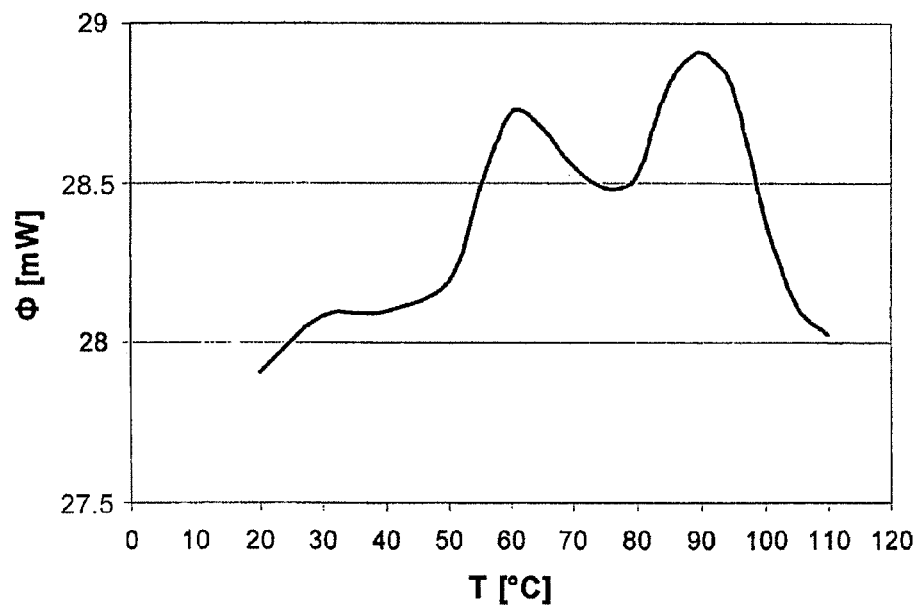
FIG. 2 represents a DSC curve of a PVA gel which has been produced according to example 2 of the invention.

The gel PVA 92 was produced by an analogous method as in Example 1, wherein, however, the proportion of PVA2 in relation to PVA1 and PVA2 was 31.4%, the water content was nominally 62.9 and actually, as a result of evaporation losses in production, was 59.1, and no filler was used. The viscosity of the gel after melting at 100° C. and after 5 min storage at 60° C. was 190 Pas. The gel was then stored for 4 weeks at room temperature and then examined by means of DSC. The DSC curve is represented in FIG. 2. The test piece weight was 18.37 mg, the heating speed was 10° C./min and two peaks were established with peak temperatures at 59.9 and 92.1

Example 3

Figure 3:
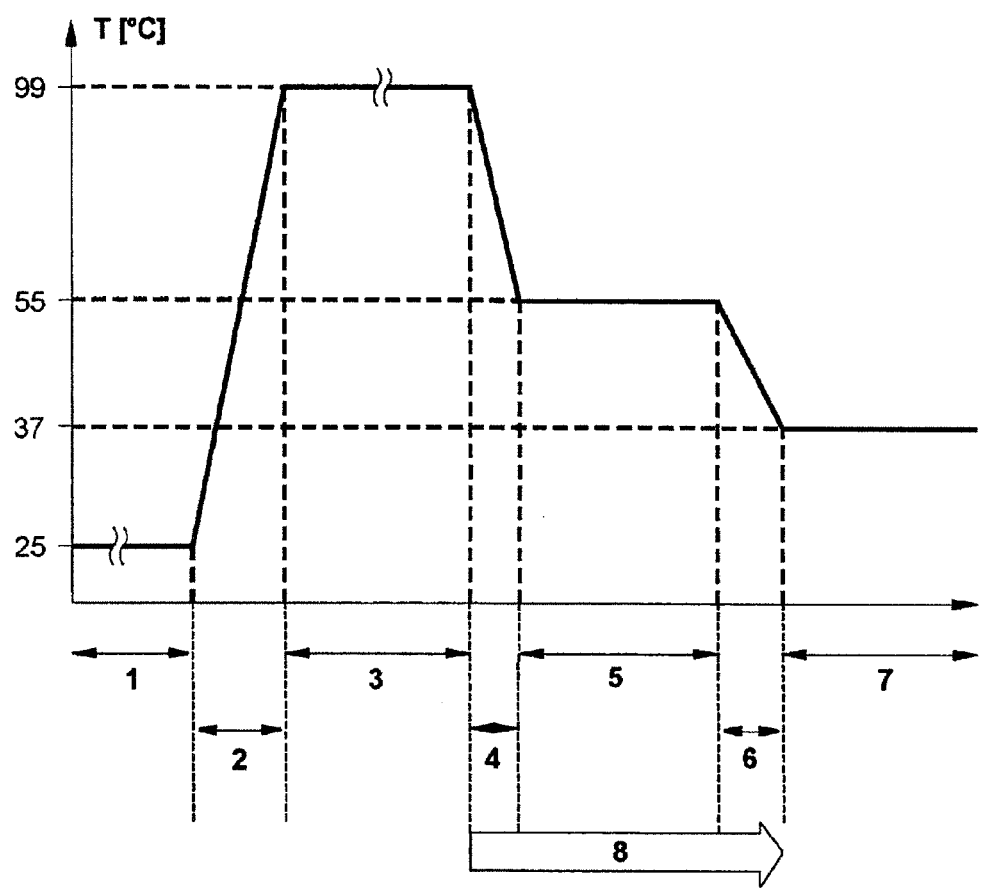
FIG. 3 shows exemplarily the different applied temperature stages starting from the transport and storage of a PVA gel according to the invention in a solid state up to a step of reaching its desired solidity in the body after injection.

FIG. 3 shows how a PVA gel according to the invention is transported and stored in the solid state (typically for weeks to months, 1). Shortly before the operation, the gel is liquefied for a short period (typically for 5 min-15 min) at temperatures typically to 95° C.-99° C., 2). At temperatures below the boiling point of water, relevant excess pressures never occur in the gel which is to be melted, which makes less requirements with regard to the tightness of the respective vessel. At increased temperature (over approximately 80° C., typically at 95° C.-99° C.) the melted but sealed gel can be stored over a longer period (up to several hours) for further processing (3).

As soon as the injection of the gel is shortly to be carried out, in accordance with the course of surgery, (typically no more than 5 minutes), as rapid a cooling of the gel as possible is initiated to a temperature which is compatible with the body (typically to 50° C.-60° C., 4). After transfer into a syringe, the injection into the body can begin (e.g. into the intervertebral disc, the vertebral body, etc., 5). After injection into the body, the gel cools down to 37° C. body temperature (6) and in so doing becomes increasingly more solid. After reaching the desired solidity, the gel assumes its permanent function as a mechanical implant (7).

The processing interval (8) is critical in terms of time and must therefore be carried out within a predetermined time span (typically within 5 min-15 min).

Figure 4:
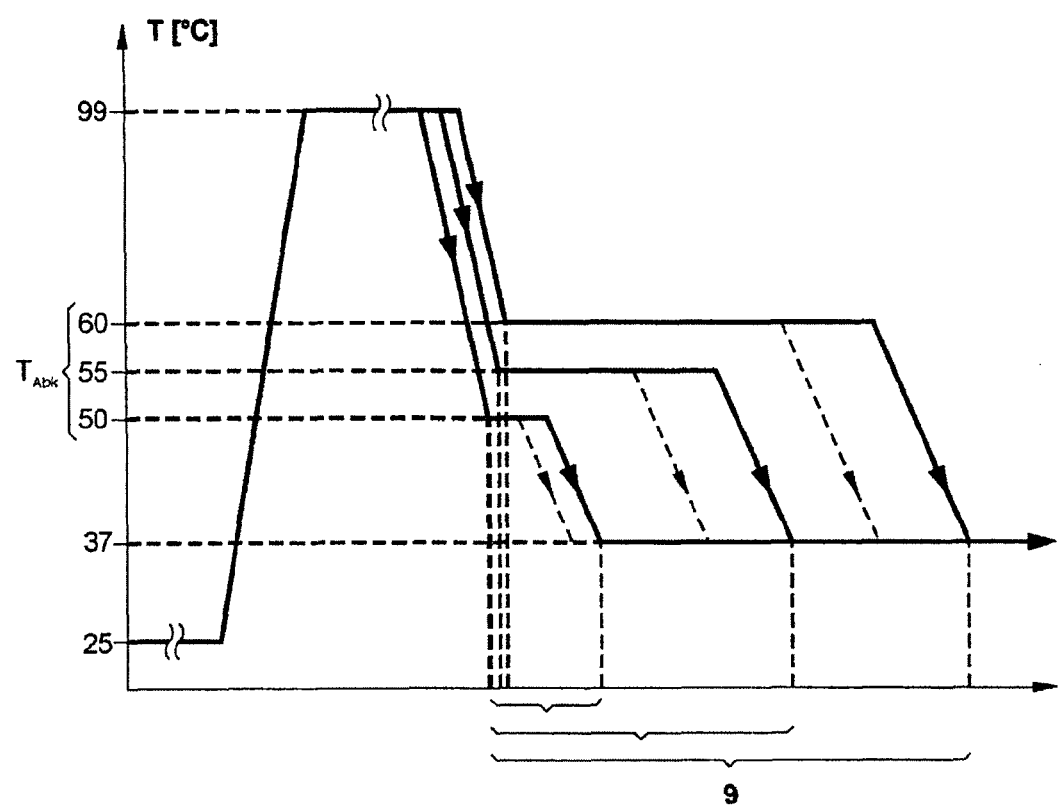
FIG. 4 shows the dependency of the maximum possible time being available for the injection of a PVA gel according to the invention into the body on a temperature $T_{Abk}$.

With the initiation of the cooling (4) to a temperature which is compatible with the body $T_{Abk}$, a time-critical phase begins for the melted PVA gel. FIG. 4 shows that the maximum possible time (9) which is available for the injection (5) depends greatly on $T_{Abk}$. Variations of a few ° C. (typically +/−2° C.-5° C.) can extend or shorten the processing time by several minutes. This dependence can be used to optimize the processing time (5) from practical points of view of surgery. Normally, this should be approximately 5 min-15 min, but, if required could be varied in a much wider range (e.g. 10 sec-60 min).

Figure 5:
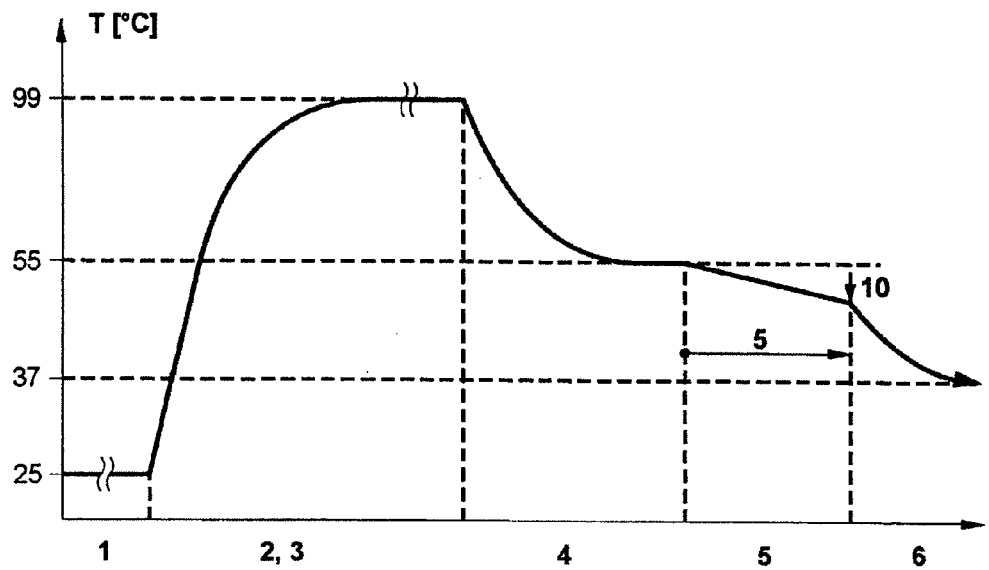
FIG. 5 describes a mode of operation of an apparatus using heating elements (or cooling elements) with a fixed temperature for achieving the different applied temperature stages which are necessary for the preparation and injection of a PVA gel according to the invention.

The different applied temperature stages which are necessary for the preparation and injection of the PVA gel are achieved by an apparatus which is provided specifically for this. FIG. 5 describes the mode of operation of an apparatus, which uses heating elements (or cooling elements) with a fixed temperature (e.g. stabilized electrical heating source, cooling unit, Peltier element, water bath). The respective target temperature of the gel is reached slowly and asymptotically.

Figure 6:
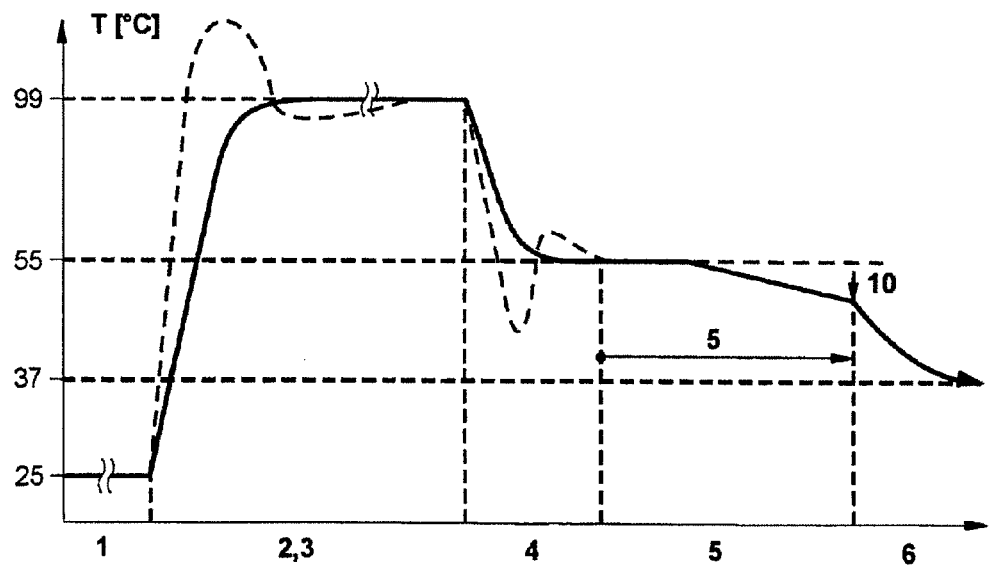
FIG. 6 describes a mode of operation of an apparatus with intelligent temperature regulation.

FIG. 6 on the other hand describes the mode of operation of an apparatus with intelligent temperature regulation. Owing to active regulation with excessive temperature of the heating element (or cooling element), the respective target temperature is reached more quickly. This can be achieved for example by an electronic control circuit with feedback of the temperature actual value and with a corresponding active readjustment in order to reach the desired value as quickly as possible. Likewise, a good insulation of the heated gel in the injection syringe with respect to the ambient temperature results in a smaller temperature drop (10) of the gel during the injection time (5). The combined advantage of the more rapid reaching of the injection temperature owing to intelligent temperature regulation, and the good insulation of the heated gel in the syringe is a longer maximum injection time (5) with as uniform a viscosity as possible of the gel which is to be injected.

Example 4

Figure 7:
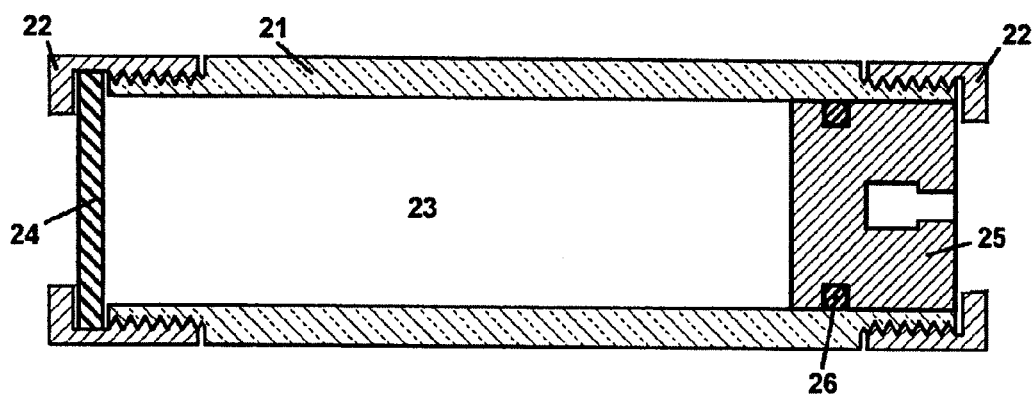
FIG. 7 shows an ampoule for storage and for transportation of a PVA gel according to the invention.

The PVA gel is kept for longer storage and for transportation before use in a (sterile) ampoule (20) which is closed in as water-tight and gas-tight a manner as possible. This is shown in FIG. 7. The filling is to be as complete as possible here, but in particular is to be free of air bubbles. The ampoule (20) is preferably intended for disposable use and has a cylindrical shape. Ideally, the ampoule (20) is manufactured from a transparent material (21) so that its contents can be monitored visually. End caps (22) on one or both sides have a screw- or snap closure.

The ampoule is constructed so that it can be used both for the storage and transportation of the gel (23), closed in a water- and gas-tight manner, for the initial melting of the gel and for the subsequent injecting of the gel into the body under high pressure (up to 20 MPa). For this multiple purpose, the ampoule (20) is designed as a type of hermetically sealed, (sterile) pre-filled syringe.

One side of the ampoule (20) has a rubber membrane (24) (similar to that which an ampoule usually requires for the repeated drawing of medicaments into a syringe), which is pierced centrally for the pressing out of the gel from the ampoule with the cannula. The other side of the ampoule is closed by a slidingly sealed plunger (25) (ring seal (26) or O-ring). The end cap (22) prevents the plunger (25) from being pressed out from the ampoule (positive stop). After insertion of the ampoule into the syringe (40), the plunger (25) can be pushed forwards through the central hole of the end cap (22) with a threaded shaft (41), whereby the gel is pressed out from the ampoule. The threaded shaft engages here in the hole of the plunger, so that on turning of the threaded shaft in the opposite direction, the plunger can also be drawn back again.

Figure 8:
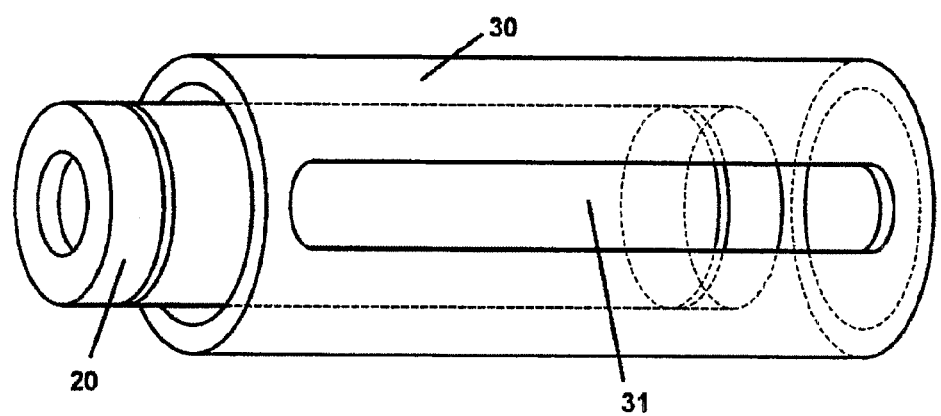
FIG. 8 shows a tube for receiving an ampoule according to the invention.

FIG. 8 shows an approximately equally long tube (30), the inner diameter (ID) of which is only just larger than the outer diameter (OD) of the ampoule (20), which is made from a material with good heat storing properties (e.g. brass, copper). The wall of the tube (30) is approximately 2 mm-5 mm thick. For better heat storage of the gel, the heated ampoule is kept inside the similarly temperature-regulated tube. One or more longitudinal slits (31) on the tube allow an inspection of the filling level of the ampoule (20). The tube serves in addition as mechanical reinforcement of the (thin-walled) ampoule, so that the latter can withstand greater internal pressures (up to 20 MPa) without intensive deformation (e.g. radial convexity).

Figure 9:
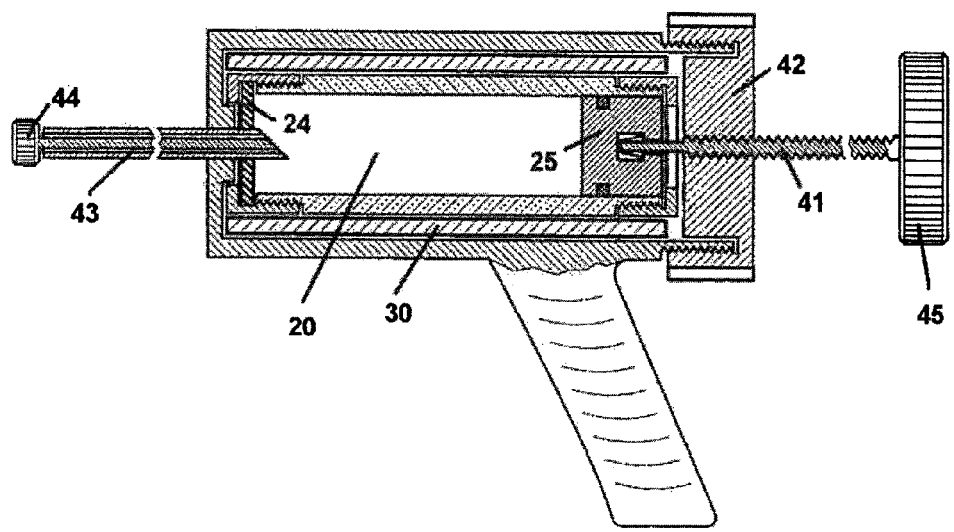
FIG. 9 shows an injection device according to the invention with an ampoule used in a tube.

FIG. 9 shows how the ampoule (20), heated and then cooled to injection temperature, is used in the tube (30), which is likewise pre-heated to injection temperature (or pre-heated to a few ° C. thereabove). Both are inserted from the rear into the screwed-on syringe (40) (screw cap (42) was removed).

A cannula (43), mounted concentrically on the front end of the syringe (40) projects by approximately 5 mm-10 mm into the interior of the syringe. An inner insert (44) ("trocar"), which is inserted from the front into the cannula, additionally splints the cannula internally and also prevents its clogging. The part of the cannula projecting in the interior of the syringe is sharpened obliquely and has cutting edges. On placing and tightening of the screw cap (42), which is placed from the rear, the rubber membrane (24) of the hermetically sealed ampoule (20) is pierced by the sharpened cannula (43).

The threaded shaft (41), which is guided by the central threaded hole of the screw cap, is pushed forward by the knurled manual rotary knob (45), until it engages in the corresponding central recess of the movable plunger (25). After the inner insert (44) has been removed from the cannula, the ampoule (20) with the movable plunger (25) can be pressed out through the (long) cannula (43) with the manual rotary knob (45). The required cannula length and thickness is dependent on the locality of the injection. For a typical application for the injecting of gel into the human intervertebral disc or into the human vertebral body, the cannula (43) is between 10 cm and 15 cm long, and is between approximately 2 mm and 5 mm thick. The required pressures in order to press the relatively highly viscous gel out through a long and thin cannula are high, typically from approximately 1 MPa to 20 MPa.

Figure 10:
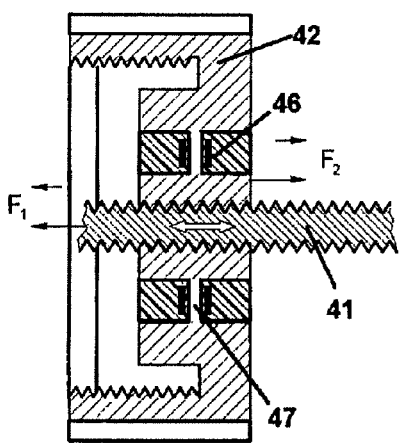
FIG. 10 describes a force measurement by means of strain gauges, which are applied to the invention in the screw cap of an injection device according to the invention on a thin bridge for measuring the pressure during the injection of the PVA gel.
Figure 11:
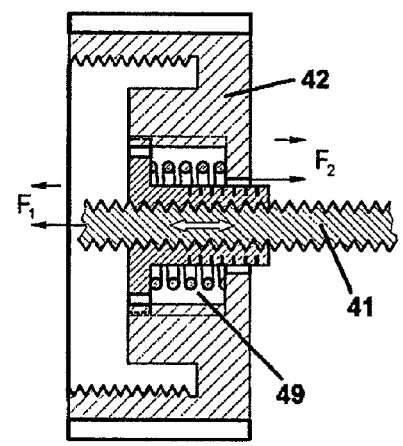
FIG. 11 describes a purely mechanical measurement device using a compression spring in the screw cap of an injection device according to the invention for measuring the pressure during the injection of the PVA gel.

A pressure measurement during the injecting of the gel is desirable for various reasons. The correct mode of operation of the syringe (40) can be monitored continuously. Pressures which are too great, which endanger the structural strength of the syringe, can be prevented. The uniform filling of a cavity in the body (e.g. a cleared intervertebral disc) can be standardised with the filling pressure. FIGS. 10 and 11 show how such a pressure measurement can be incorporated for example in the interior of the screw cap.

The axial force which is transferred via threaded pin (41) of the syringe (40) onto the sliding plunger (25) of the ampoule (20), is proportional to the pressure produced in the ampoule. The screw cap (42) therefore lends itself to measuring the axial force $F_1$ on the threaded pin (41) simply and directly (as reactive force $F_2$). FIG. 10 describes a force measurement by means of strain gauges (SG) (46), which are applied in the screw cap (42) on a thin bridge (47). A SG pair lie respectively opposite each other, so that one measures extension and the other measures compression. Two SG pairs are interconnected to a temperature-compensated full bridge (Wheatstone bridge). The resulting electrical signal (mV) is proportional to the force, but must usually be electrically amplified and individually calibrated for the respective measurement bridge. However, the measurement is precise, has a good resolution and the measurement device is very rigid in axial direction.

FIG. 11 is purely mechanical and therefore needs neither a voltage source nor an electronic circuit. A compression spring (48) is compressed with axial load onto the screw cap (42). An internal part of the screw cap (42), which is secured against rotation by a groove, serves as an abutment for the threaded pin (41). When the spring (48) is shortened by the threaded pin (41), the internal part of the screw cap pushes itself increasingly forward relative to the outer screw cap. The compression force can be read directly by means of a calibrated graduation on the internal part. The purely mechanical measurement device is much less rigid in axial direction than that in FIG. 10, which makes the controlled and finely dosed ejection of the highly viscous gel from the ampoule considerably more difficult.

A device with two heating elements (A and B) serves for the controlled heating and cooling of the ampoule which is filled with PVA gel, and of the heat-storing tube fitting therewith. The heating- and cooling elements (e.g. Peltier elements, electrical heating elements and cooling units) can be activated individually. A temperature sensor, arranged for example on the base of a recess and therefore in direct contact respectively with the inserted ampoule or the tube, serves for the feedback of the actual temperature. A temperature control compares the actual temperature with the desired temperature.

The simple operator surface starts with a button the initial heating and melting of the gel in the ampoule. A display (optical and/or acoustic) signals the reaching of the melting temperature and hence the readiness for use of the gel for imminent injecting. The cooling of the gel can be initiated by a further button before the injecting. From now on, the further procedure is time-critical.

After reaching the injection temperature, a display indicates the possible start of the injection process. The ampoule is now removed from the heating device and together with the heat-storing tube is inserted into the syringe. The assembly of the syringe takes place in every case in the sterile area of the operation field. At the same time, a stopwatch begins to run backwards. As soon as the time of zero is reached, a warning display indicates that the injection must now be ended.

Figure 12:
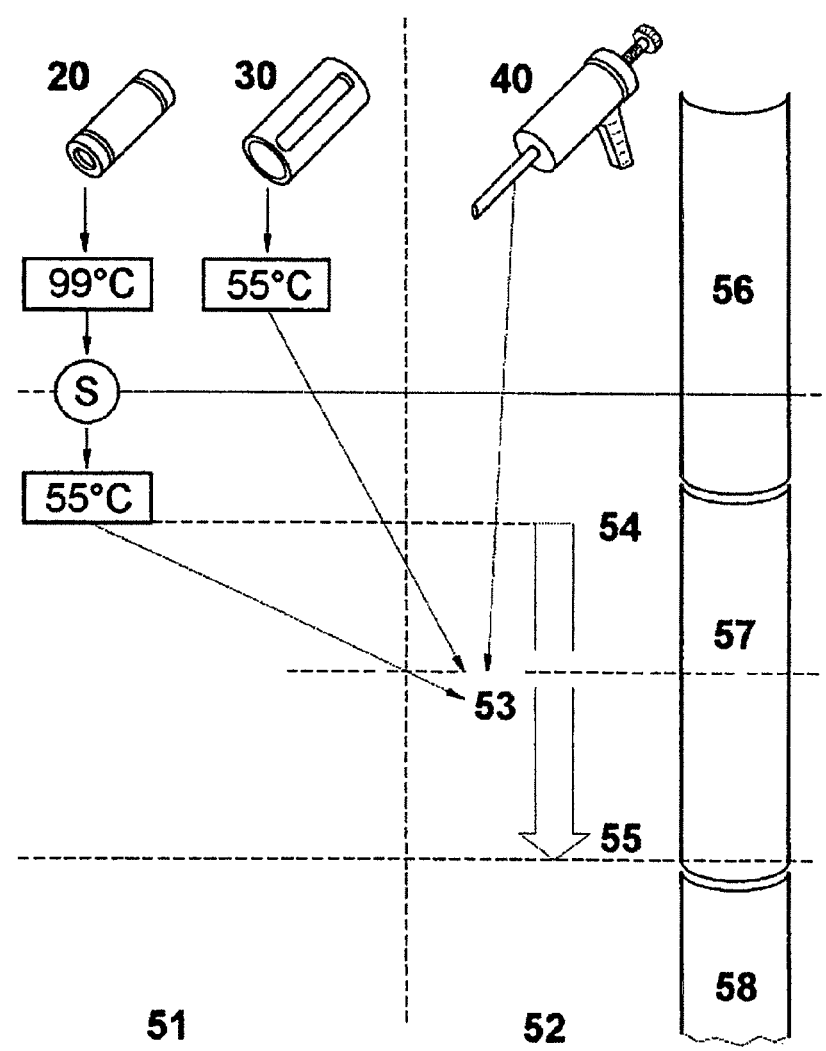
FIG. 12 is a summary of the use of a PVA gel according to the invention for injecting into a body cavity.

FIG. 12 is a summary of the use of the gel for injecting into a body cavity (shown here for injecting into a human intervertebral disc). Initially in the non-sterile area (51) of the operation field, the gel is melted in the ampoule (20) and the heat-storing tube (30) is brought to injection temperature (or slightly above). In the meantime, the surgical injection of the gel is prepared.

As soon as the injecting of the gel can be reliably predicted to be less than 5 min away, the controlled cooling of the gel to injection temperature is initiated (Start S). On reaching the injection temperature, the syringe (40) is charged with the gel-filled ampoule and the pre-heated tube (53) in the sterile area (52) of the operation field. The transfer of the ampoule and of the tube from the non-sterile into the sterile area can be solved in a technically simple manner, for example with the opening and tipping out of the ampoule and of the tube from an internally sterile container.

With corresponding operator guidance (stopwatch, warning display runs between start injecting (54) and stop injecting (55)), the gel can now be applied in a controlled manner during an optimally set processing time. After the processing time has elapsed, typically the cannula is to be left for a further short time in the wound (for example for 1 min to 5 min), so that on withdrawal of the cannula, the gel, which is continuing to harden, can not flow backwards.

The following steps take place here: access to the intervertebral disc, clearing of the nucleus and preparation for the injection (56), injecting and X-raying for monitoring (57) and allowing to harden and withdrawal of the cannula (58).

TABLE 1

| No. | Intervertebral disc segment | Nucleus material removed [g] | PVA gel injected [cm³] | Duration of loading [h] | Number of loading cycles | Extrusion [%] |
|---|---|---|---|---|---|---|
| 1 | T11/12 | 2.36 | 2.64 | 48 | 69,300 | 0 |
| 2 | L3/4 | 4.31 | 4.20 | 15 | 20,883 | 0* |

TABLE 1-continued

| No. | Intervertebral disc segment | Nucleus material removed [g] | PVA gel injected [cm³] | Duration of loading [h] | Number of loading cycles | Extrusion [%] |
|---|---|---|---|---|---|---|
| 3 | T12/L1 | 2.52 | 3.76 | <5 | 5,446 | 0* |
| 4 | L2/3 | 4.37 | 3.78 | 44 | 60,874 | 0 |
| 5 | L2/3 | 4.14 | 3.95 | 48 | 70,000 | 0 |

*Premature termination of the test as a result of fracture of end plates

TABLE 2

| No. | Pw1 | Pw2 | Pw | PVA1/PVA [%] | W [%] | Viscosity [Pas] |
|---|---|---|---|---|---|---|
| 2 | 2500 | 180 | 749.76 | 8.4 | 54 | 25 |
| 6 | 2500 | 180 | 870.4 | 11 | 55 | 34 |
| 7 | 2500 | 300 | 1084 | 11 | 55 | 49 |
| 8 | 2500 | 180 | 1148.8 | 17 | 60 | 27 |
| 9 | 2500 | 300 | 1348 | 17 | 60 | 45 |

The invention claimed is:

1. An application method of a polyvinyl alcohol (PVA) gel gelating in situ, wherein the method comprises:
    a) melting the PVA gel at a first temperature (1);
    b) optionally waiting at the first temperature (2);
    c) cooling the PVA gel to a second temperature (3);
    d) injecting the PVA gel into a cavity of a biological system (4); and
    e) gelating the PVA gel (5) in the cavity of the biological system,
    wherein the PVA gel comprises PVA (component i) and water (component ii) as a swelling agent, and wherein a viscosity of the melted PVA gel at a temperature in a range of 30 to 100° C. is in a range of 60 to 2000 Pas, a water content W of the PVA gel is in a range of 52 to 64% by weight, an upper limit for a weight average of a degree of polymerisation Pw of the PVA (component i) is given by a relationship of Pw=W·150−5500, and a lower limit for the weight average of the degree of polymerisation Pw of the PVA (component i) is given by a relationship of Pw=W·90−3800.

2. The application method according to claim 1, wherein the PVA gel in steps a) and b) is situated in a closed vessel, which is opened during or after step c).

3. The application method according to claim 2, wherein the step of injecting the PVA gel (4) is carried out by means of an injection device comprising:
    a cannula (43), mounted on a front side of the injection device (40), an end of which, projecting into an interior of the injection device (40), has cutting edges;
    a screw cap (42), placed on a rear side of the injection device, which has a central threaded hole;
    a threaded pin (41) which is guided through the central threaded hole of the screw cap (42);
    a manual rotary knob (45) which is arranged on the threaded pin (41);
    wherein between the front side and the rear side of the injection device (40) a cavity is formed which receives the closed vessel.

4. The application method according to claim 1, wherein the PVA gel in step a) is melted at the first temperature and the first temperature is a temperature >85° C., the PVA gel in step c) is cooled to the second temperature and the second temperature is a temperature in a range of 30 to 80° C., and the PVA gel in step d) is injected at a temperature in the range of 30 to 80° C.

5. The application method according to claim 1, wherein during the injection of the PVA gel in step d), a pressure of <20 MPa is reached.

6. The application method according to claim 1, wherein the injection of the PVA gel in step d) takes place by means of a cannula, and the cannula for the injection of the PVA gel is introduced into an annulus by means of a dilatation method.

7. The application method according to claim 1, wherein the PVA gel is used in biomedicine.

8. The application method according to claim 7, wherein the PVA gel is used in orthopaedics.

9. The application method according to claim 7, wherein the PVA gel is used in nucleus replacement of intervertebral discs.

10. The application method according to claim 4, wherein in step c), a cooling time is <30 min.

\* \* \* \* \*